United States Patent
Takahashi et al.

(10) Patent No.: US 9,566,071 B2
(45) Date of Patent: Feb. 14, 2017

(54) SYSTEMS AND DEVICES FOR CEREBRAL ANEURYSM REPAIR

(71) Applicant: Blockade Medical, LLC, Irvine, CA (US)

(72) Inventors: Randall Takahashi, Irvine, CA (US); David Ferrera, Coto de Caza, CA (US)

(73) Assignee: BLOCKADE MEDICAL, LLC, Irvine, CA (US)

( * ) Notice: Subject to any disclaimer, the term of this patent is extended or adjusted under 35 U.S.C. 154(b) by 321 days.

(21) Appl. No.: 14/224,390

(22) Filed: Mar. 25, 2014

(65) Prior Publication Data

US 2014/0207180 A1    Jul. 24, 2014

(51) Int. Cl.
| | | |
|---|---|---|
| A61B 17/12 | (2006.01) | |
| A61L 31/08 | (2006.01) | |
| A61L 31/18 | (2006.01) | |
| A61L 31/02 | (2006.01) | |
| A61B 17/00 | (2006.01) | |

(52) U.S. Cl.
CPC ... *A61B 17/12113* (2013.01); *A61B 17/12109* (2013.01); *A61B 17/12145* (2013.01); *A61B 17/12154* (2013.01); *A61L 31/022* (2013.01); *A61L 31/088* (2013.01); *A61L 31/18* (2013.01); *A61B 2017/00893* (2013.01); *A61B 2017/1209* (2013.01); *A61B 2017/12063* (2013.01); *A61B 2090/3966* (2016.02); *A61L 2430/36* (2013.01)

(58) Field of Classification Search
CPC .................. A61B 17/12022; A61B 17/12027; A61B 17/12031; A61B 17/12036; A61B 17/12099; A61B 17/12109; A61B 17/12113; A61B 17/12118; A61B 17/12131; A61B 17/1214; A61B 17/12145; A61B 17/12168; A61B 17/12172; A61B 2017/1205; A61B 2017/12054; A61B 2017/12063; A61B 2017/1209; A61L 2430/36

See application file for complete search history.

(56) References Cited

U.S. PATENT DOCUMENTS

| | | | |
|---|---|---|---|
| 4,994,069 A | | 2/1991 | Ritchart et al. |
| 5,891,128 A | * | 4/1999 | Gia ................. A61B 17/12022 606/1 |
| 5,984,929 A | * | 11/1999 | Bashiri ............ A61B 17/12022 606/108 |

(Continued)

OTHER PUBLICATIONS

International Search Report and Written Opinion for PCT/US2014/033881 mailed on Aug. 27, 2014, (13 pages).

(Continued)

*Primary Examiner* — Ryan J Severson
(74) *Attorney, Agent, or Firm* — Patnstr, APC; Peter Jon Gluck

(57) ABSTRACT

An embolization device for treating ischemic stroke is disclosed, having a surface, wherein the body portion is configured to have a radiopaque and electropositive surface under physiological conditions when the device is emplaced, which ionically binds a blood component in an amount effective to promote stability of device in situ to bind to a tissue component in an amount effective to increase adhesion of the device as compared to a device without an electropositive surface. Embolic coils being so delivered are electrolytically detachable in under 10 seconds, according to the disclosed vascular implant systems.

7 Claims, 5 Drawing Sheets

(56) References Cited

U.S. PATENT DOCUMENTS

| | | | |
|---|---|---|---|
| 6,123,714 A * | 9/2000 | Gia | A61B 17/12022 606/1 |
| 6,165,178 A * | 12/2000 | Bashiri | A61B 17/12022 606/1 |
| 6,425,893 B1 | 7/2002 | Guglielmi | |
| 6,458,127 B1 | 10/2002 | Truckai et al. | |
| 6,468,266 B1 * | 10/2002 | Bashiri | A61B 17/12022 606/1 |
| 6,589,230 B2 * | 7/2003 | Gia | A61B 17/12022 606/1 |
| 7,208,172 B2 | 4/2007 | Birdsall et al. | |
| 7,645,292 B2 | 1/2010 | Porter | |
| 8,002,822 B2 * | 8/2011 | Glocker | A61L 31/088 623/1.42 |
| 8,152,839 B2 | 4/2012 | Buiser et al. | |
| 8,221,483 B2 * | 7/2012 | Ford | A61B 17/12022 606/198 |
| 8,974,513 B2 * | 3/2015 | Ford | A61B 17/12022 606/198 |
| 2001/0049521 A1 * | 12/2001 | Gia | A61B 17/12022 606/1 |
| 2003/0014073 A1 * | 1/2003 | Bashiri | A61B 17/12022 606/200 |
| 2005/0187466 A1 * | 8/2005 | Glocker | A61L 31/088 600/431 |
| 2006/0116716 A1 | 6/2006 | Gerberding | |
| 2006/0127443 A1 | 6/2006 | Helmus | |
| 2006/0282112 A1 * | 12/2006 | Griffin | A61B 17/12022 606/200 |
| 2007/0036905 A1 | 2/2007 | Kramer | |
| 2007/0073334 A1 * | 3/2007 | Ramzipoor | A61B 17/12022 606/200 |
| 2007/0100414 A1 * | 5/2007 | Licata | A61F 2/95 623/1.11 |
| 2009/0024154 A1 * | 1/2009 | Williams | A61B 17/12022 606/191 |
| 2009/0062726 A1 * | 3/2009 | Ford | A61B 17/12022 604/57 |
| 2009/0177261 A1 * | 7/2009 | Teoh | A61B 17/12022 623/1.11 |
| 2010/0094395 A1 * | 4/2010 | Kellett | A61B 17/12022 623/1.11 |
| 2010/0121350 A1 * | 5/2010 | Mirigian | A61B 17/12022 606/142 |
| 2010/0234872 A1 * | 9/2010 | Guo | A61B 17/12022 606/191 |
| 2012/0209310 A1 | 8/2012 | Chen et al. | |
| 2012/0271344 A1 * | 10/2012 | Ford | A61B 17/12022 606/200 |
| 2014/0207180 A1 * | 7/2014 | Ferrera | A61L 31/088 606/200 |
| 2015/0066073 A1 * | 3/2015 | Ma | A61B 17/1214 606/200 |
| 2015/0182227 A1 * | 7/2015 | Le | A61B 17/12113 606/200 |

OTHER PUBLICATIONS

International Search Report for PCT/US2014/031666 with a date of mailing of Aug. 4, 2014, (4 pages).

\* cited by examiner

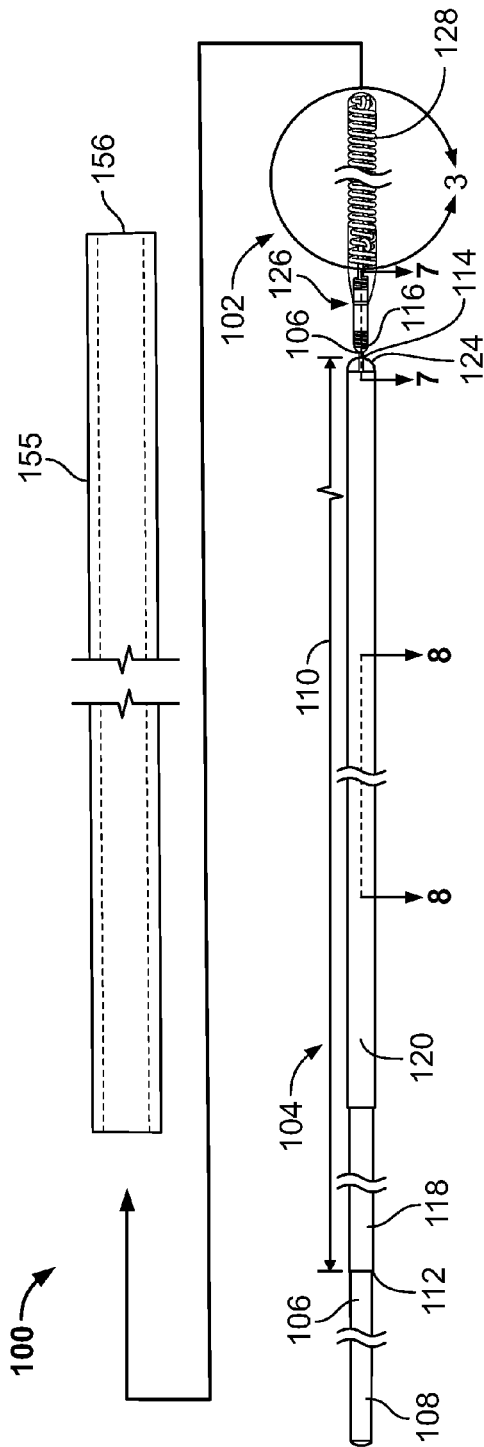
FIG. 7
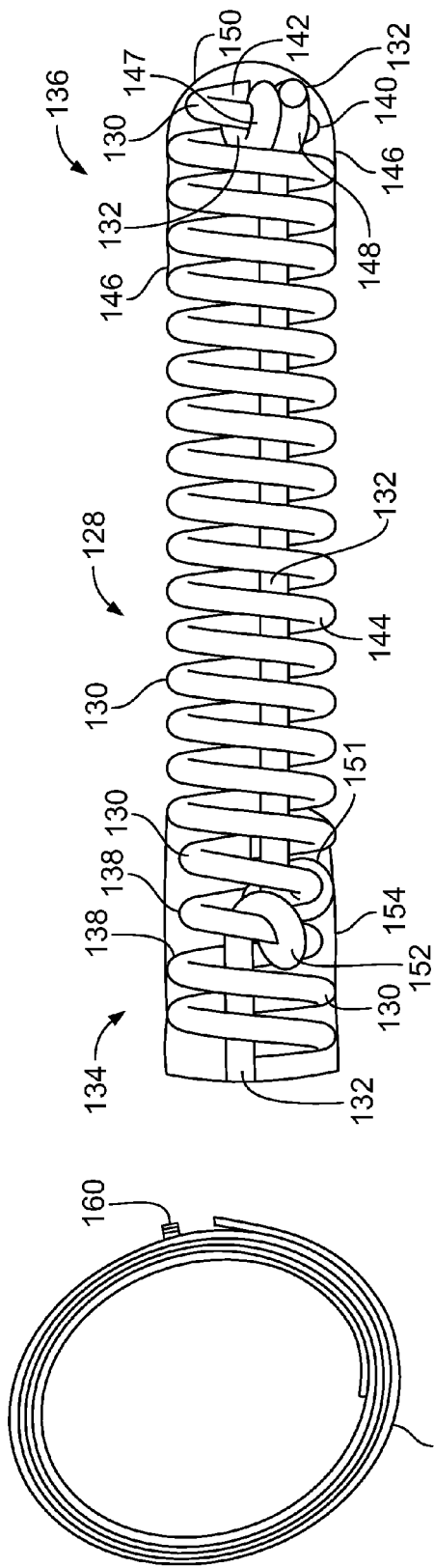
FIG. 9
FIG. 8

SYSTEMS AND DEVICES FOR CEREBRAL ANEURYSM REPAIR

CROSS-REFERENCE TO RELATED APPLICATION

This application claims the full Paris Convention priority of, and expressly incorporates by this reference U.S. provisional patent application 61/811,055, filed on Apr. 11, 2013, U.S. provisional patent application No. 61/888,240, filed Oct. 8, 2013, U.S. provisional patent application No. 61/917,854, filed Dec. 18, 2013, International Application No. PCT/US2005/020667, filed Jun. 13, 2005, International Application No. PCT/US2014/031666, filed Mar. 25, 2014, and U.S. Pat. No. 8,002,822, issued Aug. 23, 2011, the contents of which are incorporated by this reference, as if fully set forth herein in their entirety.

FIELD OF INVENTIONS

The field of the invention is compositions, devices, and methods of devices to repair cerebral aneurysms, especially as it relates to cerebral arterial repair of aneurysms, embolization of vascular abnormalities, most particularly neurovascular treatment of cerebral aneurysms.

BACKGROUND

The background description includes information that may be useful in understanding the present invention. It is not an admission that any of the information provided herein is prior art or relevant to the presently claimed invention, or that any publication specifically or implicitly referenced is prior art.

Cerebral aneurysms occur in approximately 2% of the population. Approximately 30,000 aneurysms are treated annually in the USA. Within this therapy group, 23,000 aneurysms are embolized with coils while 7,000 are repaired endoluminally with flow diverting devices. Aneurysms grow from a weakness in a blood vessel. About 80% of aneurysms are less than 8 mm with the remainder growing to as large as 40 mm. During stent-assisted coiling, a stent (Boston Scientific's Neuroform® brand of device or J&J Cordis Enterprise® brand of device) structure is placed within the artery of the vessel with the aneurysm in an attempt to reconstruct the vessel wall at the neck of the aneurysm. Patients are typically anti-coagulated and anti-aggregated with a combination of aspirin and Plavix to mitigate the thrombo-embolic effects of a foreign body response.

However, patients with sub-arachnoid hemorrhage (SAH) are typically not candidates for stents due the prophylactic drug regimen to mitigate the thrombo-embolic complications. A second approach is to perform balloon-remodeling. In this technique, a very soft, conformable balloon (for example, the eV3 Hyperform® brand of device) typically is used for balloon-test-occlusion being placed in the artery at the neck to reconstruct the neck at the aneurysm origin.

However, during this technique, flow arrest is performed while the balloon is inflated. There is a risk of initiating an ischemic event during balloon remodeling and/or a thrombo-embolic event during flow arrest. Once both these techniques are performed, coil embolization of the aneurysm can be performed. During the stenting procedure, the stent may be permanently implanted. During balloon remodeling, the balloon is removed once embolization is completed. Coils thus remain state-of-the-art treatment.

In addition, devices discussed so far, are typically visualized by markers at both the distal and proximal ends only. Although these markers verify the placement and/or deployment of the devices within the artery in relation to the abnormality to be repaired, verification of the complete opening or apposition to the artery wall or aneurysm neck cannot be verified unless a contract enhanced CT is performed. The ability to visualize these devices implanted in the artery offers procedural and clinical safety and benefit. The instant teachings address this need.

In most cases, complete embolization of the aneurysm with currently known devices will typically require at least several coils and devices, and/or are incomplete treatment of the aneurysm because the wall apposition and neck reconstruction of the aneurysm neck is insufficient and the coils previously placed have moved, or the visualization of the neck reconstruction was non-existent and the physician was unable to verify the proper placement of embolization devices at the aneurysm neck. The difficulties of stabilizing known devices within an aneurysm or vesicle are multiplied when aneurysm necks are wide, or the inflow zone of the aneurysm is in a high shear area (e.g., at a curve or bifurcation).

Further, it is not uncommon that sufficient amounts of devices cannot be placed into the aneurysm without losing microcatheter access due to aneurysm, aneurysm neck or vesicle morphology. Additionally, currently known devices can often not readily be stabilized within the aneurysm due to their visibility, softness and inertness. Finally, electrolytic detachment needs to be managed efficiently with proper timing for embolic coil delivery. Times ranging between 5 and 14 seconds of detachment time are optional for systems as discussed herein.

Thus, there is still a need for improved devices and methods of embolization devices, and especially neurovascular embolization devices for cerebral aneurysms, which are electrolytically detachable.

SUMMARY OF THE DISCLOSURE

The present inventive subject matter is drawn to compositions, devices, and methods of embolization devices that have a significantly improved implantation behavior, and especially methods and devices that are entirely visualized allowing improved delivery and retention of devices in the aneurysm or vesicle requiring occlusion. According to embodiments, contemplated devices include a body portion having a surface, wherein the body portion has a radiopaque electropositive surface under physiological conditions when the device is implanted into an aneurysm or vesicle.

Such surface is contemplated to be sufficiently radiopaque and electropositive such as to promote visualization and ionic binding of one or more blood and/or tissue components (and especially albumin) to an extent that the device is immobilized in the aneurysm or vesicle and/or coagulation around the device is stimulated. Among other suitable surfaces, it is especially preferred that the surface is modified with a radiopaque electropositive metal (in metallic form, ionic form, or oxide form), and particularly suitable metals include tantalum, calcium, copper, magnesium, potassium, silver, and sodium. Likewise, organic cationic compounds are also contemplated (and especially include carbonium cations, ammonium cations, and oxonium cations).

Consequently, the inventor contemplates methods of forming an embolization device that includes a step of providing an embolization device having a body portion with a surface. In another step, the surface is treated such that the surface is electropositive under physiological conditions when the device is implanted into an artery, an aneurysm or vesicle, wherein the surface is sufficiently electropositive such that the surface ionically binds a physiologic component in an amount effective to promote stability in the artery, in the aneurysm or vesicle.

Consequently, and viewed from a different perspective, the inventors also contemplate methods of promoting stabilization of an embolization device deposited in an artery, an aneurysm or vesicle, in which in one step an embolization device is provided that has a body portion with a surface, whereby the surface is modified with a composition that renders the surface radiopaque and electropositive under physiological conditions when the device is implanted into an artery, an aneurysm or vesicle, wherein the composition is present in an amount effective to ionically bind a physiologic component in an amount effective to promote stability of physiologic components in the artery, aneurysm or vesicle. Alternatively, the body portion is already formed from a material that renders the surface radiopaque and electropositive under physiological conditions when the device is implanted into an artery, aneurysm or vesicle, wherein the surface is sufficiently radiopaque and electropositive composition to ionically bind a physiologic component in an amount effective to promote stability of physiologic components in an artery, the aneurysm or vesicle.

According to embodiments, there is provided An embolization device, comprising a body portion having a surface, wherein the body portion is configured to have a radiopaque and electropositive surface under physiological conditions when the device is implanted into an artery, aneurysm or vesicle; and, wherein the surface is sufficiently visualized and electropositive such that the surface ionically binds a blood component in an amount effective to promote stability of device in the artery, aneurysm or vesicle, or to bind to a tissue component in an amount effective to increase adhesion of the device as compared to a device without electropositive surface.

According to embodiments, there is provided a method of forming an embolization device, comprising providing an embolization device having a body portion with a surface; treating the surface such that the surface is electropositive under physiological conditions when the device is implanted into an aneurysm or vesicle; and, wherein the surface is sufficiently electropositive such that the surface ionically binds a blood component in an amount effective to promote stability of devices in the artery, aneurysm or vesicle, or to bind to a tissue component in an amount effective to increase adhesion of the device as compared to a device without electropositive surface.

According to embodiments, there is provided A vascular implant system comprising, in combination an implant assembly including an elongate pushing member having a proximal end and a distal end, an implant coupled to the distal end of the elongate pushing member, and an electolytically detachable zone proximate the distal end of the elongate pusher member, the electrolytically detachable zone comprising a stainless steel wire having a diameter at the electrolytically detachable zone of between at least about 0.0015" and about 0.0025" and an having an electrolytically detachable zone length of between at least about 0.002" and 0.008", wherein the implant is configured to be electrolytically detachable from elongate pushing member at the electrolytically detachable zone; and an electrical power supply configured to electrically couple to the implant assembly at the proximal end of the elongate pushing member, the electrical power supply having a voltage of between about 11.5V and about 17.0V and configured to operate at a current between about 1.4 mA and about 2.4 mA.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 7 is a side elevation view of a vasoocclusive implant system according to an embodiment of the present invention.

FIG. 8 is a perspective view of a protective shipping tube for the vasoocclusive implant system of FIG. 1.

FIG. 9 is a detailed view of a distal tip portion of the vasoocclusive implant system of FIG. 7, taken from within circle 3.

DETAILED DESCRIPTION OF THE DISCLOSURE

The inventor has discovered that embolization devices with improved implantation characteristics, and especially with improved radiopacity, retention of implants and/or biocompatibility, can be prepared by inclusion of a radiopaque, electropositive surface on the device, wherein the surface is sufficiently electropositive such that the surface ionically binds one or more physiologic components in an amount effective to promote stability of physiologic components in the artery, aneurysm or vesicle, or to bind to a tissue component in an amount effective to increase adhesion of the device as compared to a corresponding device without radiopaque, electropositive surface. While not limiting to the inventive subject matter, it is especially preferred that the radiopaque, electropositive surface is provided by a radiopaque, electropositive metal that is coupled to the body of the embolization device.

Figure 1:
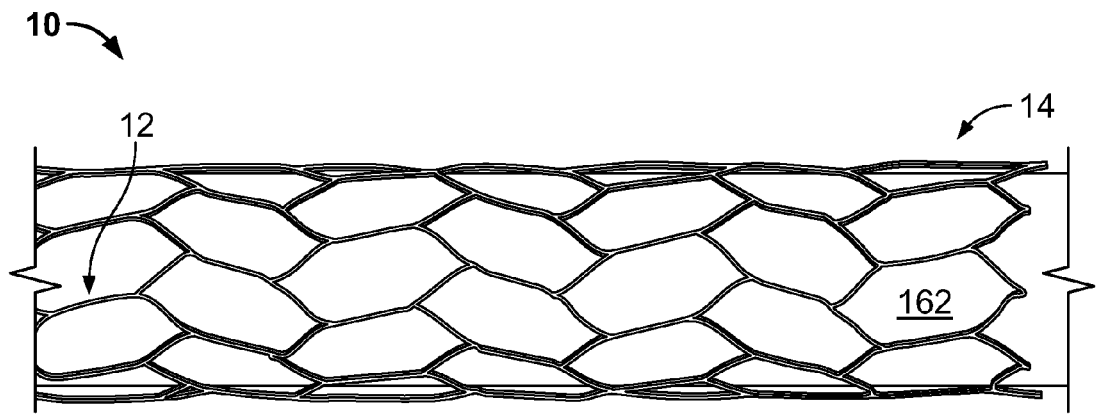
FIG. 1 is a perspective view of an exemplary aneurysm embolization device according to the inventive subject matter.
Figure 2:
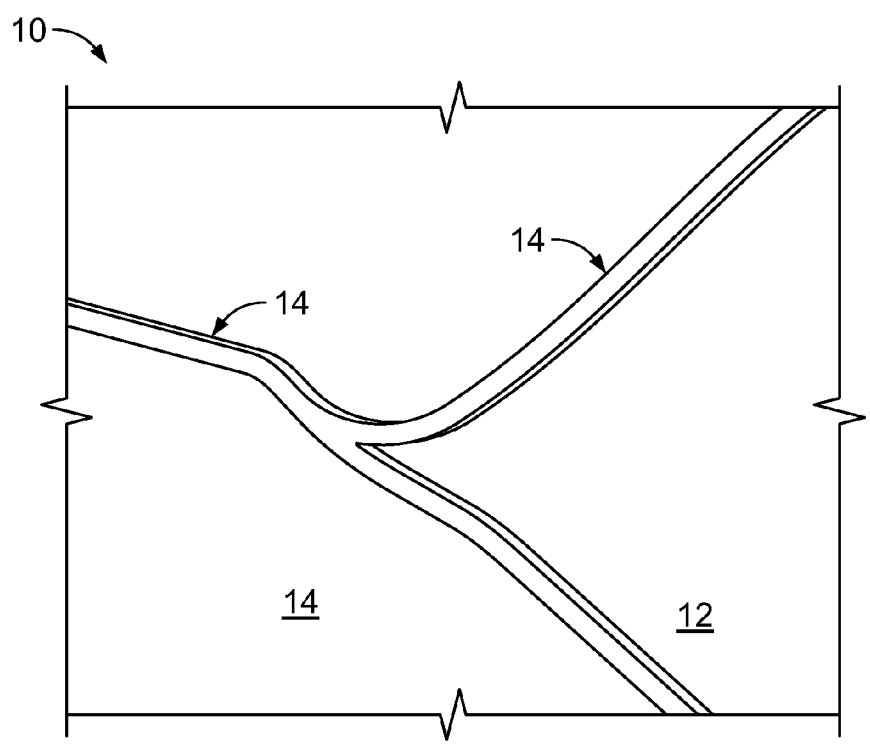
FIG. 2 is a close-up side view of the aneurysm embolization device strut bridge of FIG. 1.

FIG. 1 and FIG. 2 provide exemplary illustrations of the inventive subject matter, depicting an embolization device 10 having a surface 12 that is coated with a tantalum coating 14. The coating 14, is coupled to the surface of embolization device 12, cell 162 is defined by geometric shape desired and has a coated surface. In further detail, and still referring to the embodiments of FIG. 1 and FIG. 2, the embolization device surface 12 has sufficient width and surface area to apply a tantalum coating, when device diameter is, for example, from at least 2.0 to 5.0 mm and length is 1 cm to 5 cm. The tantalum coating 14 is radiopaque and positively charged to be visualized the entire length and attract and ionically interacts with negatively charged bodily fluids such as cells, blood, elements such as oxygen or tissue to the embolization device surface 12 creating a stable placement to maintain embolization device location and position. Of course, it should be noted that the radiopaque electronegative metal need not provide an immediate positive charge, but may be initially present as a metallic electroneutral metal.

Upon contact with electrolyte, body fluid, or tissue, a redox reaction may occur (or may be induced) that converts the electroneutral material into a positively charged surface. Such redox reaction may be entirely due to the chemical components present in the body fluid or tissue, or may be induced by added chemicals or during an external (pre-implantation) redox process. Thus, it should be noted that the electropositive surface might be in truly ionic form, or present as a metal oxide (e.g., tantalum pentoxide) that acts as an intermediate conductor. Alternatively, and especially where the metal is converted to a metal oxide, it should be noted that the binding interaction between the metal oxide and the tissue/body fluid may also be due to hydrogen bonds, hydrophilic interaction, and even via apatite-type reaction.

While not wishing to be bound by any particular theory or hypothesis, the inventor contemplates that the most common type of ionic bonding is seen in compounds of metals and nonmetals. Certain metals, such as tantalum, are characterized by having a small number of electrons in excess of a stable, closed-shell electronic configuration. As such, they have the tendency to lose these extra electrons in order to attain a stable configuration. This property is known as electropositivity. When a highly electropositive metal such as tantalum is combined with a highly electronegative nonmetal, such as bodily tissue and fluids, the extra electrons from the metal, tantalum, atoms are transferred to the electron-deficient nonmetal atoms in the bodily tissue or fluid. This reaction produces metal cations and nonmetal anions, which are attracted to each other to form an ionic compound.

Further construction details of the devices according to the inventive subject matter are shown in FIG. 1 and FIG. 2 in which the embolization device 10 is made of nitinol, (or any other suitable material, including stainless steel, tungsten, cobalt-chromium, etc.). Further, the various components of the embolization device 10 can be made of different materials.

Figure 3:
FIG. 3 is a perspective view of an exemplary aneurysm embolization device according to the inventive subject matter.
Figure 4:
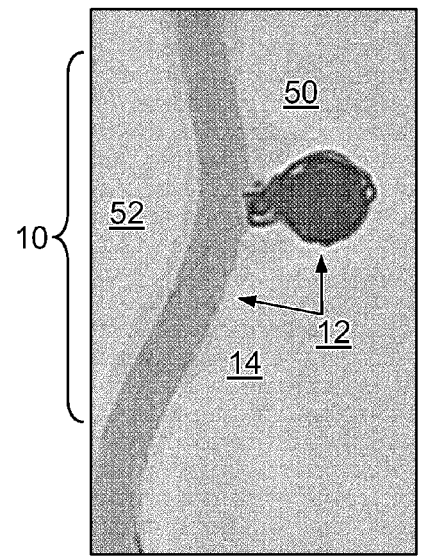
FIG. 4 is a side view of the aneurysm embolization device of FIG. 3.
Figure 5:
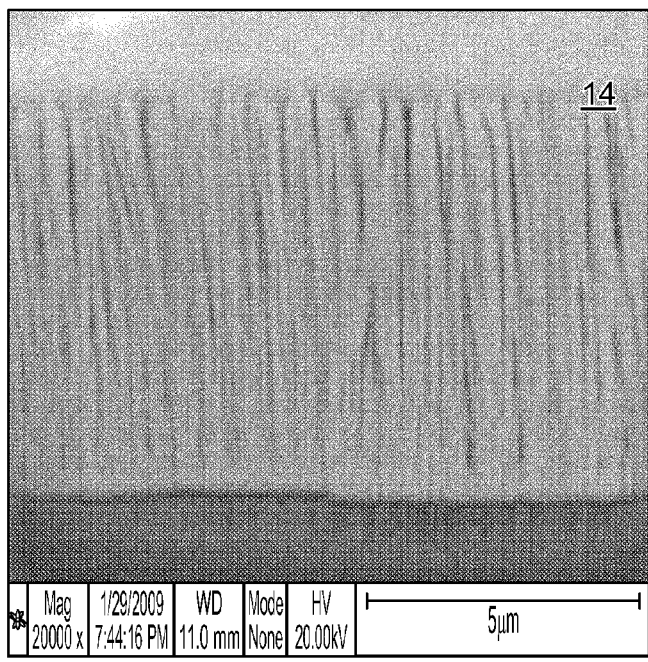
FIG. 5 is an electron micrograph (cross section) of an exemplary embolization device with a tantalum layer according to the inventive subject matter.
Figure 6:
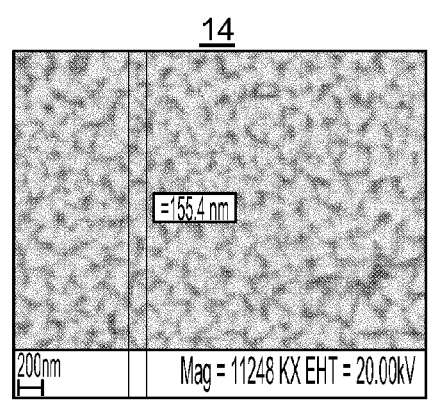
FIG. 6 is an electron micrograph (top view) of an exemplary embolization device with a tantalum layer according to the inventive subject matter.

Referring now to FIG. 3 and FIG. 4, there are shown prior art embolization devices 69 (hard to see), in situ. In contrast, the instant device is shown in FIG. 4 having an open cell 52. In more detail, the embolization device 10 as shown includes multi-sided cells 62 that allow microcatheters to be placed through the embolization device 10 with a surface modified with tantalum 12. In further detail, and again referring to FIG. 3 and FIG. 4, the multi-sided cell 52 is sufficiently wide to allow guidewires, microcatheters such as about 1 to 3 mm. The construction details of FIG. 3 and FIG. 4 are that the embolization device 50 may be made of nitinol or of any other sufficient material such as stainless steel, tungsten, cobalt-chromium, and the like. As noted before, the various components of the embolization device 50 can be made of different materials.

FIG. 7 illustrates a vasoocclusive implant system 100 comprising microcoil implant 102 detachably coupled to a pusher member 104. The pusher member 104 includes a core wire 106, extending the length of the pusher member 104, and made from a biocompatible material such as stainless steel, for example 304 series stainless steel. The core wire 106 diameter at a proximal end 108 may be between 0.008" and 0.018", and more particularly between 0.010" and 0.012. " An electrically insulated region 110 of the pusher member 104 extends a majority of the core wire 106 length, between a first point 112, approximately 10 cm from the extreme proximal end of the core wire 106 and a second point 114, near the distal end 116 of the core wire 106. Directly covering the surface of the core wire 106 is a polymeric coating 118, for example PTFE (polytetrafluoro ethylene), Parylene or polyimide, and having a thickness of about 0.00005" to about 0.0010", or more particularly 0.0001" to 0.0005". A polymeric cover tube 120 is secured over the core wire 106 and the polymeric coating 118. The polymeric cover tube 120 may comprise polyethylene terephthalate (PET) shrink tubing that is heat shrunk over the core wire 106 (and optionally, also over the polymeric coating 118) while maintaining a tension of the ends of the tubing. The core wire 106 may have transition zones, including tapers, where the diameter decreases from its diameter at the proximal end 108 to a diameter of, for example, 0.005" to 0.006" throughout a portion of the electrically insulated region 110 of the pusher member 104. The diameter of the core wire 106 at the distal end 116 may be 0.002" to 0.003, " including the portion of the distal end 116 that is outside of the electrically insulated region 110 of the pusher member 104. A tip 124 may be applied to the polymeric cover tube 120 in order to complete the electrically insulated region 110.

The microcoil implant 102 is detachably coupled to the pusher member 104 via a coupling joint 126. FIG. 9 illustrates a coil assembly 128 of the microcoil implant 102 (shortened for sake of easier depiction). An embolic coil 130 may be constructed of platinum or a platinum alloy, for example 92% platinum/8% Tungsten, and close wound from wire 144 having a diameter between 0.001" and 0.004, " or more particularly between 0.00125" to 0.00325. " The coil may have a length (when straight) of between 0.5 cm and 50 cm, or more particularly between 1 cm and 40 cm. Prior to assembly into the microcoil implant 102, the embolic coil 130 is formed in to one of several possible shapes, as described in more detail in relation to FIGS. 10-12.

In order to minimize stretching of the embolic coil 130 of the microcoil implant 102, a tether 132 is tied between a proximal end 134 and a distal end 136 of the embolic coil 130. The tether 132 may be formed of a thermoplastic elastomer such as Engage® brand of material, or a polyester strand, such as diameter polyethylene terephthalate (PET). The diameter of the tether 132 may be 0.0015" to 0.0030", or more particularly 0.0022" for the Engage strand. The diameter of the tether 132 may be 0.00075" to 0.0015, " or more particularly 0.0010" for the PET strand. The primary outer diameter of the embolic coil 130 may be between 0.009" and 0.019. " In order to secure the tether at the proximal end 134 and distal end 136 of the embolic coil 130, a two reduced diameter portions 138, 140 are created in certain winds of the embolic coil 130, for example by carefully pinching and shaping with fine tweezers. The end 142 of the reduced diameter portion 140 is trimmed and the tether 132 is tied in one or more knots 146, 148, around the wire 144 of the reduced diameter portion 140. A tip encapsulation 146 comprising an adhesive or an epoxy, for example, an ultraviolet-curable adhesive, a urethane adhesive, a ready-mixed two-part epoxy, or a frozen and defrosted two-part epoxy, is applied securing the one or more knots 147, 148 to the reduced diameter portion 140, and forming a substantially hemispherical tip 150.

With a sufficient amount of slack/tension placed on the tether 132, the tether is tied in one or more knots 151, 152 to the reduced diameter portion 138. A cylindrical encapsulation 154, also comprising an adhesive or an epoxy, is applied, securing the one or more knots 151, 152 to the reduced diameter portion 138. The cylindrical encapsulation 154 provides electrical isolation of the embolic coil 130 from the core wire 106, and thus allows for a simpler geometry of the materials involved in the electrolysis during detachment. The tether 132 serves as a stretch-resistant member to minimize stretching of the embolic coil 130. In a separate embodiment, the tether 132 may be made from a multi-fiber or stranded polymer or a microcable.

Turning again to FIG. 7, an introducer tube 155, having an inner lumen 156 with a diameter slightly larger than the maximum outer diameter of the microcoil implant 102 and pusher member 104 of the vasoocclusive implant system 100 is used to straighten a shaped embolic coil 130, and to insert the vasoocclusive implant system 100 into a lumen of a microcatheter. The vasoocclusive implant system 100 is packaged with and is handled outside of the patient's body within the inner lumen 156 of the introducer tube 155. The vasoocclusive implant system 100 and introducer tube 155 are packaged for sterilization by placing them within a protective shipping tube 158. The proximal end 108 of the pusher ember 104 is held axially secure by a soft clip 160.

Figure 10:
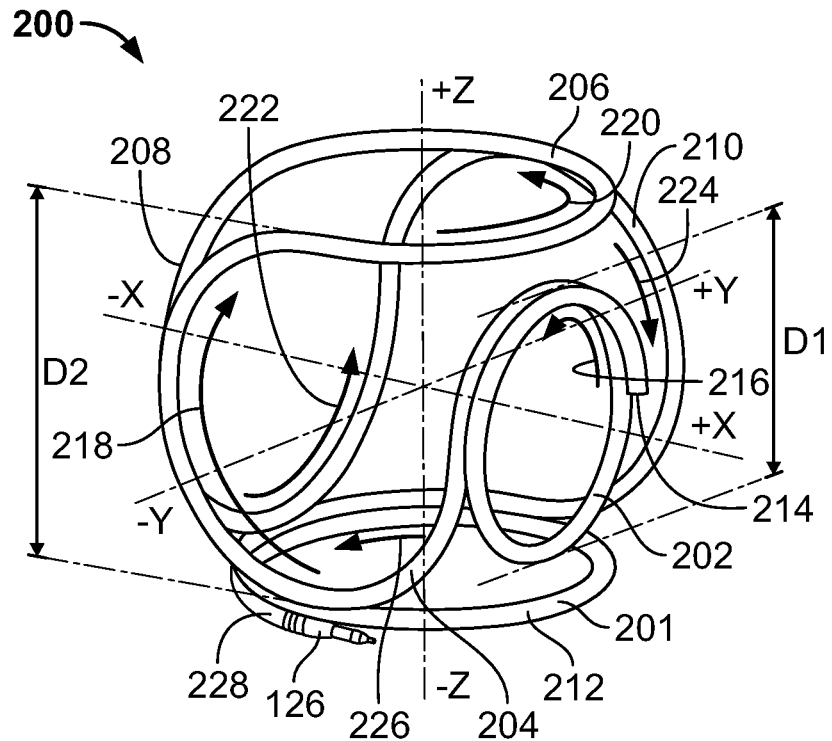
FIG. 10 is a perspective view of a vasoocclusive implant according to one embodiment of the invention.
Figure 11:
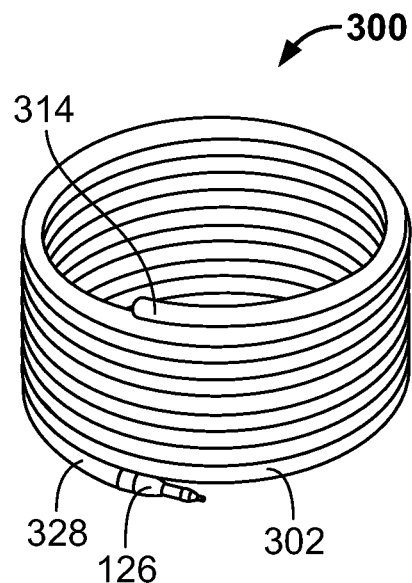
FIG. 11 is a perspective view of a vasoocclusive implant according to another embodiment of the invention.
Figure 12:
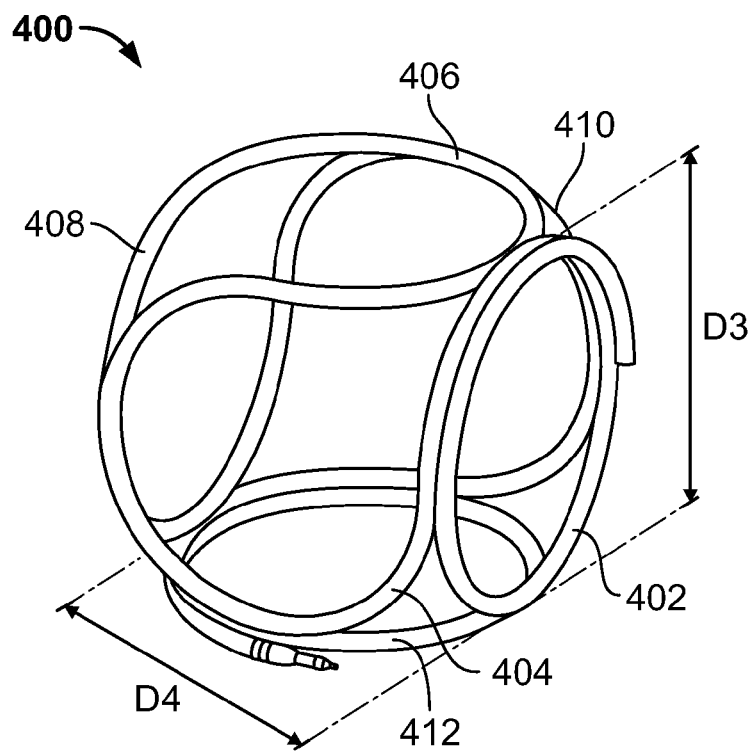
FIG. 12 is a perspective of a vasoocclusive implant according to another embodiment of the invention.

FIGS. 10-12 illustrate vaoocclusive implants according to embodiments of the invention. FIG. 10 illustrates a framing microcoil implant 200 made from an embolic coil 201, and having a box shape which approximates a spheroid when placed within an aneurysm. Loops 202, 204, 206, 208, 210, 212 are wound on three axes: an X-axis extending in the negative direction (−X) and a positive direction (+X) from a coordinate origin (O), a Y-axis extending in the negative direction (−Y) and a positive direction (+Y) from the coordinate origin (O), and an Z-axis extending in the negative direction (−Z) and a positive direction (+Z) from the coordinate origin (O). A first loop 202 having a diameter Di begins at a first end 214 of the embolic coil 201 and extends around the +X-axis in a direction 216. As depicted in FIG. 10, the first loop 202 includes approximately 1 Vi revolutions, but may (along with the other loops 204, 206, 208, 210, 212) include between Vi revolution and 10 revolutions. The second loop 204 having a diameter D2 continues from loop 202 and extends around the −Y-axis in a direction 218. The third loop 206 then extends around the +Z-axis in a direction 220. The fourth loop 208 then extends around the −X-axis in a direction 222. The fifth loop 210 then extends around the +Y-axis in a direction 224. And finally, the sixth loop 212 extends around the Z-axis in a direction 226. As seen in FIG. 10, subsequent to the forming of the loops 202, 204, 206, 208, 210, 212, the coupling joint 126 is formed at a second end 228 of the embolic coil 201.

This framing microcoil implant 200 is configured for being the initial microcoil placed within an aneurysm, and therefore, in this embodiment, loops 204, 206, 208, 210, and 212 all have a diameter approximately equal to D2. The first loop 202, however, is configured to be the first loop introduced into the artery, and in order to maximize the ability of the microcoil implant 200 to stay within the aneurysm during coiling, the diameter Di of the first loop 202 is to between 65% and 75% of the diameter D2, and more particularly, about 70% of the diameter of D2. Assuming that D2 is chosen to approximate the diameter of the aneurysm, when the first loop 202 of the microcoil implant 200 is inserted within the aneurysm, as it makes its way circumferentially around the wall of the aneurysm, it will undershoot the diameter of the aneurysm if and when it passes over the opening at the aneurysm neck, and thus will remain within the confined of the aneurysm. Upon assembly of the microcoil implant 200 into the vasoocclusive implant system 100, the choice of the tether 132 can be important for creating a microcoil implant 200 that behaves well as a framing microcoil, framing the aneurysm and creating a supportive lattice to aid subsequent coiling, both packing and finishing.

For example, the tether 132 may be made from 0.0009" diameter PET thread in microcoil implants 200 having a diameter D2 of 5 mm or less, while the tether 132 may be made from 0.0022" diameter Engage® brand of thread in microcoil implants 200 having a diameter D2 of 5 mm or more. In addition, the diameter of the wire 144, if 92/8 Pt/W, may be chosen as 0.0015" in 0.011" diameter embolic coils 130 and 0.002" in 0.012" diameter embolic coils 130. The 0.011" embolic coils 130 may be chosen for the construction of microcoil implants 200 having a diameter D2 of 4.5 mm or less, and the 0.012" diameter embolic coils 130 may be chosen for the construction of microcoil implants 200 having a diameter D2 of 4.5 mm or more.

In microcoil implants 200 having a diameter D2 or 6 mm or larger, additional framing microcoil models may be made having 0.013" or larger embolic coils 130 wound with 0.002"and larger wire 144. It should be noted that the coiling procedure need not necessarily use only one framing microcoil, and that during the implantation procedure, one or more framing microcoils may be used to set up the aneurysm for filling microcoils and finishing microcoils.

FIG. 11 illustrates a filling microcoil implant 300 having a helical shape. The filling microcoil implant 300 is manufactured in a similar winding and setting technique as the framing microcoil implant 200, but the helical loops 302 of the filling microcoil implant 300 are wound on a single cylindrical mandrel (not shown). The framing microcoil implant 200 is formed from an embolic coil 130 having a first end 314 and a second end 328. The tether 132 (FIG. 9) of the filling microcoil implant 300 can be constructed from a variety of materials, including a thermoplastic elastomer such as Engage®. The diameter of the tether 132 formed from Engage may range from 0.002" to 0.00275" and more particularly, may be 0.0022".

The wire 144 used in making the embolic coil 130 used to construct the filling microcoil implant 300 may be 92/8 Pt/W wire of a diameter between about 0.00175" and 0.00275", and more particularly between 0.002" and 0.00225". The outer diameter of the embolic coil 130 of the filling microcoil implant 300 may be between 0.011"and 0.013", more particularly about 0.012". One or more filling microcoil implants 300 can be used after one or more framing coil implants 200 have been placed in the aneurysm, to pack and fill as much volume of the aneurysm as possible. The comparatively soft nature of the filling microcoil implants 300 allows a sufficient amount of packing to achieve good thrombosis and occlusion, without creating potentially dangerous stresses on the wall of the aneurysm that could potentially lead to rupture (or re-rupture). In addition to the use of a helically shaped microcoil as a filling microcoil implant 300, they may also be used as a finishing microcoil implant, which is the last one or more implant that are placed at the neck of the aneurysm to engage well with the coil mass while maximizing the filled volume at the neck of the aneurysm. These finishing microcoils are typically smaller, having an outer diameter of about 0.010", and being wound from 92/8 Pt/W wire having a diameter of between 0.001" to 0.00175", more particularly between 0.00125" and 0.0015". The tether 132 used in a helical finishing microcoil may comprise 0.001" PET thread.

FIG. 12 illustrates a complex microcoil implant 400, having a first loop 402, second loop 404, third loop 406, fourth loop 408, fifth loop 410, and sixth loop 412, wound in three axes, much like the microcoil implant 200 of FIG. 10. However, the Diameter D3 of the first loop 402 is about the same as the diameter D4 of each of the other loops 404, 406, 408, 410, 412. Therefore the mandrel 500 used in the construction of the loops 402, 404, 406, 408, 410, 412 would include a first arm 502 having a similar diameter to the other arms 504, 506, 508, 510, 512. A complex microcoil implant 400 of this construction may be used as a framing microcoil implant, but may alternatively by used as a finishing microcoil implant. The complex or three-dimensional structure in many clinical situations can aid in better engagement of the finishing microcoil implant with the rest of the coil mass, due to its ability to interlock. There is thus less chance of the finishing microcoil implant migrating out of the aneurysm, into the parent artery.

The treatment of ruptured and unruptured intracranial aneurysms with the use of transluminally-delivered occlusive microcoils has a relatively low morbidity and mortality rate in comparison with surgical clipping. However, there are still many drawbacks that have been reported. Microcoils are typically delivered into the aneurysm one at a time, and it is of critical importance that each microcoil be visible, for example by fluoroscopy, and that if a microcoil is not delivered into a desirable position, that if may be safely and easily withdrawn from the aneurysm. A microcatheter is placed so that its tip is adjacent the neck of the aneurysm, and the microcoils are delivered through the lumen of the microcatheter. Microcatheter design, placement, and tip orientation are all important factors in determining how well the microcatheter will support the delivery, and if needed, removal, of the microcoil to and from the aneurysm. If excessive resistance is met during the delivery of the microcoil, the microcatheter may "back out," thus losing its supporting position and/or orientation in relation to the aneurysm. One complication that may occur during microcoil delivery or removal is the actual stretching of the winds of the microcoil. For example, if the microcoil is pulled into the microcatheter while the microcatheter is in a position that causes its tip to place a larger than desired force on a portion of the microcoil, the microcoil may not slide into the microcatheter easily, and an axially-directed tensile force may cause a significant and permanent increase in the length of the microcoil. The microcoil will then have permanently lost its mechanical characteristics and suffered from a decrease in radiopacity in the stretched area.

Coil stretching of this nature can be expensive to the neurointerventionalist performing the procedure, as this microcoil will need to be discarded and replaced, but it may also interfere with the procedure, as stretched coils may also be prone to being trapped, breaking, or inadvertently interlocking with other microcoils, already placed within the aneurysm. There is also the possibility of causing other microcoils that were already placed within the aneurysm to migrate out of the aneurysm, into the parent artery, a severe complication.

Placement of a first "framing" microcoil within an aneurysm is often done using a three-dimensional, or "complex" microcoil (a microcoil which is wound around a plurality of axes). The initial framing microcoil is the base structure into which later "filling" microcoils are packed. As the first microcoil placed into a completely uncoiled aneurysm, even if it is a three-dimensional or complex microcoil, the first loop of the microcoil may exit from the aneurysm after it has entered, instead of looping several times around the inside of the aneurysm. This is exacerbated by the absence of a prior microcoil, whose structure tends to help subsequently placed coils stay within the aneurysm. Microcoils in which all loops are formed at substantially the same diameter are especially prone to this exiting phenomenon when used as the first framing microcoil.

Microcoils may migrate out of the aneurysm either during the coiling procedure, or at a later date following the procedure. The migrated loop or loops of the microcoil can be a nidus for potentially fatal thromboembolism. The migration of portions of microcoils may be due to incomplete packing of the microcoil into the coil mass within the aneurysm.

Additionally, incomplete packing of microcoils, particularly at the neck of the aneurysm, may cause incomplete thrombosis, and thus leave the aneurysm prone to rupture, or in the case of previously ruptured aneurysms, re-rupture. Certain aneurysms with incomplete microcoil packing at the neck may nevertheless initially thrombose completely. However, they may still be prone to recanalization, via the dynamic characteristics of a thromboembolus. Compaction of the coil mass with the aneurysm is another factor which may cause recanalization. The inability to pack enough coil mass into the aneurysm, due to coil stiffness or shape is a possible reason for an insufficient coil mass.

FIG. 7 illustrates a vasoocclusive implant system 100 comprising microcoil implant 102 detachably coupled to a pusher member 104. The pusher member 104 includes a core wire 106, extending the length of the pusher member 104, and made from a biocompatible material such as stainless steel, for example 304 series stainless steel. The core wire 106 diameter at a proximal end 108 may be between 0.008" and 0.018", and more particularly between 0.010" and 0.012". An electrically insulated region 110 of the pusher member 104 extends a majority of the core wire 106 length, between a first point 112, approximately 10 cm from the extreme proximal end of the core wire 106 and a second point 114, near the distal end 116 of the core wire 106. Directly covering the surface of the core wire 106 is a polymeric coating 118, for example PTFE (polytetrafluoro ethylene), Parylene or polyimide, and having a thickness of about 0.00005" to about 0.0010", or more particularly 0.0001" to 0.0005". A polymeric cover tube 120 is secured over the core wire 106 and the polymeric coating 118. The polymeric cover tube 120 may comprise polyethylene terephthalate (PET) shrink tubing that is heat shrunk over the core wire 106 (and optionally, also over the polymeric coating 118) while maintaining a tension of the ends of the tubing. A marker coil 122 (FIG. 9) may be sandwiched between the core wire 106 and the polymeric cover tube 120, for example, by placing the marker coil 122 over the core wire 106 or over the polymeric coating 118, and heat shrinking or bonding the polymeric cover tube 120 over the them. The core wire 106 may have transition zones, including tapers, where the diameter decreases from its diameter at the proximal end 108 to a diameter of, for example, 0.005" to 0.006" throughout a portion of the electrically insulated region 110 of the pusher member 104. The diameter of the core wire 106 at the distal end 116 may be 0.002" to 0.003", including the portion of the distal end 116 that is outside of the electrically insulated region 110 of the pusher member 104. A tip 124 may be applied to the polymeric cover tube 120 in order to complete the electrically insulated region 110.

The microcoil implant 102 is detachably coupled to the pusher member 104 via a coupling joint 126, which is described in more detail with relation to FIG. 7. FIG. 3 illustrates a coil assembly 128 of the microcoil implant 102 (shortened for sake of easier depiction). An embolic coil 130 may be constructed of platinum or a platinum alloy, for example 92% platinum/8% Tungsten, and close wound from wire 144 having a diameter between 0.001" and 0.004", or more particularly between 0.00125" to 0.00325". The coil may have a length (when straight) of between 0.5 cm and 50 cm, or more particularly between 1 cm and 40 cm. The prior to assembly into the microcoil implant 102, the embolic coil 130 is formed in to one of several possible shapes, as described in more detail in relation to FIGS. 4-6 and FIG. 10. In order to minimize stretching of the embolic coil 130 of the microcoil implant 102, a tether 132 is tied between a proximal end 134 and a distal end 136 of the embolic coil 130. The tether 132 may be formed of a thermoplastic elastomer such as Engage®, or a polyester strand, such as diameter polyethylene terephthalate (PET). The diameter of the tether 132 may be 0.0015" to 0.0030", or more particularly 0.0022" for the Engage strand. The diameter of the tether 132 may be 0.00075" to 0.0015", or more particularly 0.0010" for the PET strand. The primary outer diameter of the embolic coil 130 may be between 0.009" and 0.019". In order to secure the tether at the proximal end 134 and distal end 136 of the embolic coil 130, a two reduced diameter portions 138, 140 are created in certain winds of the embolic coil 130, for example by carefully pinching and shaping with fine tweezers. The end 142 of the reduced diameter portion 140 is trimmed and the tether 132 is tied in one or more knots 146, 148, around the wire 144 of the reduced diameter portion 140. A tip encapsulation 146 comprising an adhesive or an epoxy, for example, an ultraviolet-curable adhesive, a urethane adhesive, a ready-mixed two-part epoxy, or a frozen and defrosted two-part epoxy, is applied, securing the one or more knots 147, 148 to the reduced diameter portion 140, and forming a substantially hemispherical tip 150. With a sufficient amount of slack/tension is placed on the tether 132, the tether is tied in one or more knots 151, 152 to the reduced diameter portion 138.

A cylindrical encapsulation 154, also comprising an adhesive or an epoxy, is applied, securing the one or more knots 151, 152 to the reduced diameter portion 138. The cylindrical encapsulation 154 provides electrical isolation of the embolic coil 130 from the core wire 106, and thus allows for a simpler geometry of the materials involved in the electrolysis during detachment. The tether 132 serves as a stretch-resistant member to minimize stretching of the embolic coil 130. In a separate embodiment, the tether 132 may be made from a multi-filar or stranded polymer or a microcable.

Figure 13:
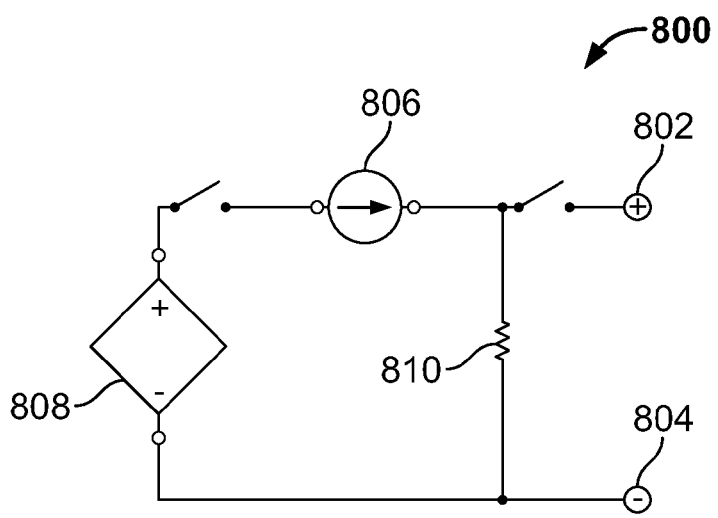
FIG. 13 is a circuit diagram of the electrical power supply coupled to an electrolytically detachable implant assembly that is inserted within a patient.

Turning to FIG. 13, a circuit diagram 800 of the electrical power supply 700 of FIG. 11, the electrode 708 is positively charged and is represented by a terminal connection 802, at which the first electrode 708 of the first clip 712 is connected to the uninsulated proximal end 108 of the core wire 106 of the pusher member 104. The electrode 710 is negatively charged and is represented by a terminal connection 804, at which the second electrode 710 of the second clip 714 is connected to a conductive needle or probe, whose tip is inserted into the patient, for example at the groin or shoulder areas. A constant current source 806 powered by a controlled DC voltage source 808 is run through a system resistor 810 and the parallel resistance in the patient, current passing through the core wire 106 and the patient, via the uninsulated detachment zone 162 (FIG. 7). As shown in the graph 900 in FIG. 13, a constant current (i) 902 is maintained over time (t), with the controlled DC voltage source 808 increasing the voltage 904 as the total resistance increases due to the electrolytic dissolution of the stainless steel at the detachment zone 162. When the detachment zone 162 is completely obliterated, the voltage 904 is forced upward in a spike 906, triggering a notification of detachment.

Those skilled in the art understand that detachment between at least about 4 and 14 seconds, are achieved by actuating the instant system. Clinically, consistent detachment times under 10 seconds have been achieved. (Blockade Medical, LLC, Irvine, Calif. 92693)

Moreover, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In one especially preferred aspect of the inventive subject matter, an embolization device has a body portion made from a metal or metal alloy known in the art of stent assisted coil embolization. For example, contemplated body portions may comprise stainless steel, titanium, nitinol, etc. The stent diameter is typically between 2.0 and 5.0 mm, the stent wall thickness is typically between 30 and 100 microns and the stent surface is coated via vapor deposition with a thin 5 to 30 micron layer of tantalum.

The advantages of the present inventive subject matter include, without limitation, that the devices contemplated herein are highly visible/radiopaque and able to attract negatively charged bodily materials to create to stable embolization of an aneurysm sac or vesicle, via direct binding, coagulation, or indirect binding. Such attraction/binding to fluids and their components, cells, tissue, proteins, is thought to be readily achieved because most of such materials are more electronegative (relative to tantalum or other electropositive materials) while tantalum is positively charged/electropositive. Further, devices according to the inventive subject matter will generally pass through most common and commercially available microcatheters without any deliverability concerns or issues as otherwise associated with standard braided stents or laser-cut tube stents. Further, the devices can easily be repositioned within the artery, aneurysm or vesicle if first placement is undesirable.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A vascular implant system, comprising, in combination:
an implant assembly including an elongate pushing member having a proximal end and a distal end, an implant coupled to the distal end of the elongate pushing member, and an electrolytically detachable zone proximate the distal end of the elongate pushing member, the electrolytically detachable zone comprising a stainless steel wire having a diameter at the electrolytically detachable zone of between about 0.0015" and about 0.0025" and having an electrolytically detachable zone length of between about 0.002" and 0.008", wherein the implant is configured to be electrolytically detachable from elongate pushing member at the electrolytically detachable zone;
an electrical power supply configured to electrically couple to the implant assembly at the proximal end of the elongate pushing member, the electrical power supply having a voltage of between about 11.5V and about 17.0V and configured to operate at a current between about 1.4 mA and about 2.4 mA, whereby electrolytic detachment is achieved in less than about 10 seconds.

2. The vascular implant system of claim 1, wherein the stainless steel wire is electrically insulated along its length except for the electrolytically detachable zone and a terminal zone at the proximal end of the elongate pushing member.

3. The vascular implant system of claim 1, wherein the electrical power supply comprises a direct current source.

4. The vascular implant system of claim 1, further comprising:
a polymeric tubular member having a proximal end and a distal end, the polymeric tubular member surrounding the stainless steel wire proximal and adjacent to the electrolytically detachable zone.

5. The vascular implant system of claim 1, further comprising:
a coating of electrically insulative material surrounding the stainless steel wire immediately adjacent the distal end of a polymeric tubing member,
wherein the coating is applied in a flowable state and then transformed into a substantially non-flowable state.

6. The vascular implant system of claim 1, further comprising:
a sterile cable configured to connect the electrical power supply to the implant assembly, the sterile cable comprising a sterile button, wherein tactile operation of the sterile button activates the electrical power supply; and, wherein tactile operation of the sterile button deactivates the electrical power supply, whereby electrolytic detachment is achieved in less than 10 seconds.

7. The vascular implant, system of claim 6, wherein the implant is a vasoocclusive coil, and a detachment time ranges from about 7 to approximately 10 seconds.

* * * * *